United States Patent

Kolasa et al.

Patent Number: 5,399,699
Date of Patent: Mar. 21, 1995

[54] INDOLE IMINOOXY DERIVATIVES WHICH INHIBIT LEUKOTRIENE BIOSYNTHESIS

[75] Inventors: Teodozyi Kolasa, Lake Villa; Pramila Bhatia; Dee W. Brooks, both of Libertyville, all of Ill.

[73] Assignee: Abbott Laboratories, Abbott Park, Ill.

[21] Appl. No.: 186,410

[22] Filed: Jan. 24, 1994

[51] Int. Cl.⁶ ............... C07D 401/02; C07D 417/02; A61K 31/425; A61K 31/47
[52] U.S. Cl. ..................... 546/174; 546/273; 548/159
[58] Field of Search ........... 546/273, 174; 548/159; 514/314, 339, 367, 365

[56] References Cited

FOREIGN PATENT DOCUMENTS 0419049 3/1991 European Pat. Off. ............ 546/174

Primary Examiner—David B. Springer
Attorney, Agent, or Firm—Jerry F. Janssen

[57] ABSTRACT

Compounds of the structure

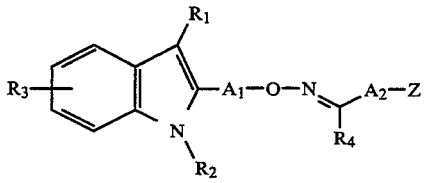

where $A_1$ is alkylene or cycloalkylene; $A_2$ is a valence bond, alkylene, or cycloalkylene; $R_1$ is selected from hydrogen, alkylthio, optionally substituted phenylthio, optionally substituted phenylalkylthio, optionally substituted 2-, 3- and 4-pyridylthio, optionally substituted 2- and 3-thienylthio, and optionally substituted 2-thiazolylthio; $R^2$ is selected from optionally substituted phenylalkyl and optionally substituted heteroarylakyl; $R^3$ is selected from alkyl, alkoxy, optionally substituted phenyl, optionally substituted phenoxy, optionally substituted phenylalkyl, optionally substituted phenylalkoxy, optionally substituted naphthyl, optionally substituted naphthyloxy, optionally substituted naphthylalkyl, optionally substituted naphthylalkoxy, optionally substituted heteroaryl, optionally substituted heteroaryloxy, optionally substituted heteroarylalkyl, and optionally substituted heteroarylalkoxy; $R^4$ is selected from hydrogen and optionally substituted alkyl; and Z is selected from —COOB, —C(OB)R⁶R⁶, —COOalkyl, —COOalkylaryl, —CONR⁵R⁶, and —COR⁶ are potent inhibitors of lipoxygenase enzymes and thus inhibit the biosynthesis of leukotrienes. These compounds are useful in the treatment of amelioration of allergic and inflammatory disease states.

4 Claims, No Drawings

INDOLE IMINOOXY DERIVATIVES WHICH INHIBIT LEUKOTRIENE BIOSYNTHESIS

TECHNICAL FIELD

This invention relates to compounds having biological activity to inhibit leukotriene biosynthesis, to pharmaceutical compositions comprising these compounds and to a medical method of treatment. More particularly, this invention concerns certain indole oxime derivatives possessing the ability to inhibit leukotriene biosynthesis, to pharmaceutical compositions comprising these compounds and to a method of inhibiting the biosynthesis of leukotrienes in humans and animal hosts in need of such treatment.

BACKGROUND OF THE INVENTION

5-Lipoxygenase is the first dedicated enzyme in the pathway leading to the biosynthesis of leukotrienes (Samuelsson, B. Leukotrienes: Mediators of Immediate Hypersensitivity Reactions and Inflammation. Science, 120: 568, 1983; Hammarstrom, S. Leukotrienes. Annual Review of Biochemistry, 52: 355, 1983). This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to $LTA_4$. This reactive leukotriene intermediate is enzymatically hydrated to $LTB_4$ or conjugated to the tripepride glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described.

Products of the 5-lipoxygenase cascade are extremely potent substances which produce a wide variety of biological effects, often in the nanomolar to picomolar concentration range. (Sirois, P. Pharmacology of the Leukotrienes. Advances in Lipid Research. R. Paoletti, D. Kritchevesky, editors, Academic Press, 21: 79, 1985.)

Leukotrienes have been reported to be important mediators in several disease states including: Asthma, Allergic Rhinitis, Rheumatoid Arthritis, Gout, Psoriasis, Adult Respiratory Distress Syndrome, Inflammatory Bowel Disease, Endotoxin Shock, Ischemia-induced Myocardial Injury, Central Nervous Pathophysiology, and Atherosclerosis The enzyme 5-lipoxygenase catalyzes the first step leading to the biosynthesis of all the leukotrienes and therefore inhibition of this enzyme provides an approach to limit the effects of all the products of this pathway. Agents capable of abrogating the effects of these potent mediators of pathophysiological processes represent a promising class of therapeutic agents (Brooks, D. W., Bell, R. L., and Carter, G. W. Chapter 8. Pulmonary and Antiallergy Agents, *Annual Reports in Medicinal Chemistry*, Allen, R. C. ed., Academic Press 1988.

Description of Prior Art

Several indole derivatives have been previously reported to have activity as leukotriene biosynthesis inhibitors. Merck Frost Canada Inc. EPA 87311031.6; Gillard, J. W. et. al. 2nd International Conference on Leukotrienes and Prostanoids in Health and Disease, Oct. 9–14, 1988, Jerusalem, Israel, Abstract S5 and recently published, J. Gillard el. al. Can. J. Physiol. Pharmacol. 1989, 67, 456–464. U.S. Pat. No. 5,190,968, Gillard and Hutchinson describes indole inhibitors of leukotriene biosynthesis. U.S. Pat. No. 5,095,031, Brooks, Carter, Dellaria, Maki, Rodriques describes indole oxime inhibitors of leukotriene biosynthesis.

SUMMARY OF THE INVENTION

In its principle embodiment, the present invention provides certain substituted indole iminooxy derivatives which exhibit unexpected activity as inhibitors of leukotriene biosynthesis and are useful in the treatment of allergic and inflammatory disease states in which leukotrienes play a role.

The present invention provides a compound of formula

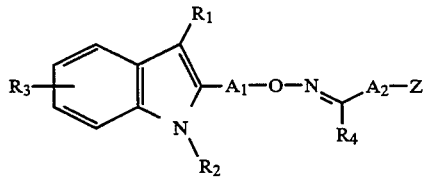

or a pharmaceutically acceptable salt thereof where $A_1$ is selected from alkenylene of one to twelve carbon atoms and cycloalkenylene of three to eight carbon atoms, $A_2$ is a valence bond or is selected from alkenylene of one to twelve carbon atoms and cycloalkenylene of three to eight carbon atoms, and $R_1$ is selected from (a) hydrogen, (b) alkylthio of one to six carbon atoms, (c) phenylthio, optionally substituted with alkyl of one to six carbon atoms, alkoxy of one to six carbon atoms, haloalkyl of one to six carbon atoms, or halogen, (d) phenylalkylthio in which the alkyl portion contains one to six carbon atoms, and the phenyl group is optionally substituted with alkyl of one to six carbon atoms, alkoxy of one to six carbon atoms, haloalkyl of one to six carbon atoms, or halogen, (e) 2-, 3- and 4-pyridylthio, optionally substituted with alkyl of one to six carbon atoms, alkoxy of one to six carbon atoms, haloalkyl of one to six carbon atoms, or halogen, (f) 2- and 3-thienylthio, optionally substituted with alkyl of one to six carbon atoms, alkoxy of one to six carbon atoms, haloalkyl of one to six carbon atoms, or halogen, and (g) 2-thiazolylthio, optionally substituted with alkyl of one to six carbon atoms, alkoxy of one to six carbon atoms, haloalkyl of one to six carbon atoms, or halogen.

$R^2$ is selected from the group consisting of phenylakyl in which the alkyl portion is of one to six carbon atoms, and heteroarylakyl in which the alkyl portion is of one to six carbon atoms, and the heteroaryl portion is selected from pyridyl, thienyl, furyl, pyrazinyl, isoquinolyl, quinolyl, imidazolyl, pyrrolyl, pyrimidyl, benzofuryl, benzothienyl, thiazolyl, and carbazolyl. In the above definition of $R^2$, the phenyl or heteroaryl group is optionally substituted with up to three substituents selected from (1) alkyl of one to six carbon atoms, (2) halogen, (3) haloalkyl of one to six carbon atoms, (4) alkoxy of one to twelve carbon atoms, (5) hydroxy, (6) carboxyalkyl of one to six carbon atoms, (7) phenyl, optionally substituted with alkyl of one to six carbon atoms, hydroxy or halogen, (8) phenoxy, optionally substituted with alkyl of one to six carbon atoms, hydroxy or halogen, (9) pyridyl, optionally substituted with alkyl of one to six carbon atoms, hydroxy or halogen, and (10) pyridyloxy, optionally substituted with alkyl of one to six carbon atoms, hydroxy or halogen.

$R^3$ is selected from (a) alkyl of one to six carbon atoms, (b) alkoxy of one to six carbon atoms, (c) optionally substituted phenyl, (d) optionally substituted phenoxy, (e) optionally substituted phenylalkyl, wherein the alkyl portion is of one to six carbon atoms, (f) optionally substituted phenylalkoxy, wherein the alkyl portion is of one to six carbon atoms, (g) optionally substituted naphthyl, (h) optionally substituted naphthyloxy, (i) optionally substituted naphthylalkyl, wherein the alkyl portion is of one to six carbon atoms, and (j) optionally substituted naphthylalkoxy, wherein the alkyl portion is of one to six carbon atoms; where the optional substituents on the phenyl or naphthyl groups are selected from (1) alkyl of one to six carbon atoms, (2) halogen, (3) alkoxy of one to six carbon atoms, (4) phenyl, optionally substituted with alkyl of one to six carbon atoms or halogen, (5) pyridyl, optionally substituted with alkyl of one to six carbon atoms or halogen, (6) thienyl, optionally substituted with alkyl of one to six carbon atoms or halogen, (7) phenoxy, optionally substituted with alkyl of one to six carbon atoms or halogen, (8) pyridyloxy, optionally substituted with alkyl of one to six carbon atoms or halogen, (9) phenylalkyl, where the alkyl portion is of one to six carbon atoms, and the phenyl group is optionally substituted with alkyl of one to six carbon atoms or halogen, (10) pyridylalkyl, where the alkyl portion is of one to six carbon atoms, and the pyridyl group is optionally substituted with alkyl of one to six carbon atoms or halogen, and (11) thienylalkyl, where the alkyl portion is of one to six carbon atoms, and the thienyl group is optionally substituted with alkyl of one to six carbon atoms or halogen, (k) optionally substituted heteroaryl, (l) optionally substituted heteroaryloxy, (m) optionally substituted heteroarylalkyl, in which the alkyl portion is of one to six carbon atoms, and (n) optionally substituted heteroarylalkoxy, in which the alkyl portion is of one to six carbon atoms; where the heteroaryl group is selected from pyridyl, thienyl, furyl, pyrazinyl, isoquinolyl, quinolyl, imidazolyl, pyrrolyl, pyrimidyl, benzofuryl, benzothienyl, thiazolyl, benzothiazolyl, and carbazolyl, where the optional substituents on the heteroaryl groups are selected from alkyl of one to six carbon atoms, halogen, alkoxy of one to six carbon atoms, and haloalkyl of one to six carbon atoms.

$R^4$ is selected from hydrogen, and alkyl of one to six carbon atoms, in which the alkyl group is optionally substituted with (1) hydroxy, (2) carboxyalkyl, where the alkyl portion is of one to six carbon atoms, (3) alkoxy, where the alkyl portion is of one to six carbon atoms, (4) phenylalkyl, where the alkyl portion is of one to six carbon atoms, and the phenyl group is optionally substituted with alkyl of one to six carbon atoms or halogen, (5) pyridylalkyl, wherein the alkyl portion is of one to six carbon atoms, and the pyridyl group is optionally substituted with alkyl of one to six carbon atoms or halogen, or (6) thienylalkyl, where the alkyl portion is of one to six carbon atoms, and the thienyl group is optionally substituted with alkyl of one to six carbon atoms, or halogen.

Z is selected from —COOB wherein B is selected from hydrogen, a phamaceutically acceptable cation, or a metabolically cleavable group; —C(OB)$R^6R^6$ where $R^6$ is hydrogen or alkyl of one to six carbon atoms; —COOalkyl where the alkyl group is of one to six carbon atoms; —COOalkylaryl where the alkyl portion is of one to six carbon atoms and the aryl portion is selected from phenyl, optionally substituted with halogen or alkyl of one to six carbon atoms, pyridyl, optionally substituted with halogen or alkyl of one to six carbon atoms, and thienyl, optionally substituted with halogen or alkyl of one to six carbon atoms; —CONR$^5$R$^6$ wherein R5 is selected from hydrogen, hydroxyl, alkyl of one to six carbon atoms, and alkoxy of one to six carbon atoms; and —COR$^6$.

In another embodiment, the present invention provides pharmaceutical compositions which comprise a therapeutically effective amount of compound as defined above in combination with a pharmaceutically acceptable carrier.

In yet another embodiment, the present invention provides a method of inhibiting leukowiene biosynthesis in a host mammal in need of such treatment comprising administering to a mammal in need of such treatment a therapeutically effective amount of a compound as defined above.

Detailed Description

As used throughout this specification and the appended claims, the following terms have the meanings specified.

The term "$C_1$-$C_6$ alkyl" refers to a monovalent group derived from a straight or branched chain saturated hydrocarbon containing from one to six carbon atoms by the removal of a single hydrogen atom. Alkyl groups are exemplified by methyl, ethyl, n- and iso-propyl, n-, sec-, iso- and tert-butyl, and the like.

The terms "$C_1$-$C_6$ alkoxy" and "$C_1$-$C_6$ alkoxyl" denote an alkyl group, as defined above, attached to the parent molecular moiety through an oxygen atom. Representative alkoxy groups include methoxy, ethoxy, propoxy, butoxy, and the like.

The terms "alkenyl" or "$C_2$-$C_6$ alkenyl" as used herein refer to a monovalent straight or branched chain group derived by the removal of a single hydrogen atom from an alkene of 2 to 6 carbon atoms including, but not limited to ethenyl, 1-propenyl, 2-propenyl, 2-methyl-1-propenyl, 1-butenyl, 2-butenyl and the like.

The terms "alkylene" or "alkylenyl" denote a divalent group derived from a straight or branched chain saturated hydrocarbon containing two to six carbon atoms by the removal of two hydrogen atoms, for example methylene, 1,2-ethylene, 1,1-ethylene, 1,3-propylene, 2,2-dimethylpropylene, and the like.

The terms "alkenylene" denotes a divalent group derived from a straight or branched chain hydrocarbon containing from two to six carbon atoms and at least one carbon-carbon double bond. Examples of alkenylene include —CH=CH—, —CH$_2$CH=CH—, —C(CH$_3$)=CH—, —CH$_2$CH=CHCH$_2$—, and the like.

The terms "alkynylene" refers to a divalent group derived by the removal of two hydrogen atoms from a straight or branched chain acyclic hydrocarbon group containing from two to six carbon atoms and a carbon-carbon triple bond. Examples of alkynylene include

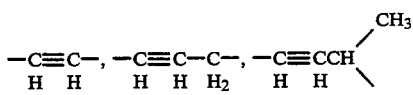

and the like.

The term "aryl" as used herein refers to substituted and unsubstituted carbocyclic aromatic groups including phenyl, 1- or 2-naphthyl, 1,2-dihydronaphthyl, 1,2,3,4-tetrahydronaphthyl wherein the aryl group may be substituted with 1, 2, or 3 substituents independently selected from halo, $C_1$ to $C_6$ alkyl, $C_1$-$C_6$ alkoxy and halosubstituted $C_1$-$C_6$ alkyl.

The term "heteroaryl" as used herein refers to substituted and unsubstituted heterocyclic groups including pyridyl, thienyl, furanyl, pyrazinyl, isoquinoyl, quinolyl, imidazolyl, pyrrolyl, pyrimidyl, benzofuryl, benzothienyl, thiazolyl, benzothiazolyl and carbazolyl wherein the heteroaryl group may be substituted with 1, 2, or 3 substituents independently selected from halo, $C_1$ to $C_6$ alkyl, $C_1$-$C_6$ alkoxy and halosubstituted $C_1$-$C_6$ alkyl.

The terms "cycloalkyl" and "$C_3$-$C_8$ cycloalkyl" as used herein refer to cyclic groups, of 3 to 8 carbons. Representative cycloalkyl groups include cyclopropyl, cyclobutyl, cyclopentyl, cyclohexyl, cycloheptyl and the like.

"Cycloalkylene" refers to a divalent group derived by the removal of teo hydrogen atoms from a saturated cyclic hydrocarbon and is represented by such groups as

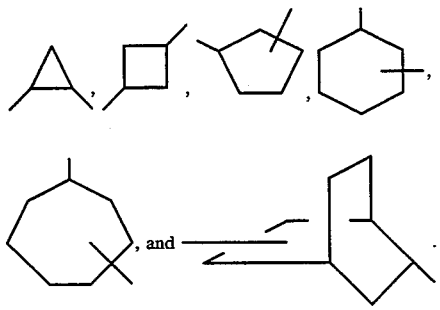

The term "haloalkyl" denotes an alkyl group, as defined above, having one, two, or three halogen atoms attached thereto and is exemplified by such groups as chloromethyl, bromoethyl, trifluoromethyl, and the like.

The term "metabolically cleavable group" denotes a group which is cleaved in vivo to yield the parent molecule of the formula I indicated above wherein M is hydrogen. Examples of metabolically cleavable groups include —COR, —COOR, —CONRR and —CH$_2$OR radicals where R is selected independently at each occurrence from alkyl, trialkylsilyl, carbocyclic aryl or carbocyclic aryl substituted with one or more of $C_1$-$C_4$ alkyl, halogen, hydroxy or $C_1$-$C_4$ alkoxy. Specific examples of representative metabolically cleavable groups include acetyl, methoxycarbonyl, benzoyl, methoxymethyl and trimethylsilyl groups.

By "pharmaceutically acceptable salt" it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Preferred Embodiments

Preferred compounds of the present invention are those having the structure

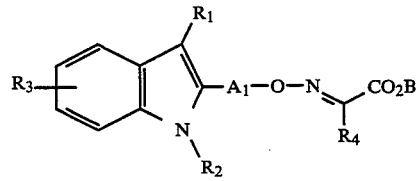

where the values of $R_1$, $R_2$, $R_3$, $A_1$, $R_4$, and B are as defined above.

Compounds contemplated as falling within the scope of the present invention include, but are not limited to:
(1-(4-chlorobenzyl)-3-(t-butylthio)-5-(2-quinolinemethoxy))indol-2-yl-(2,2-dimethyl)prop-3-yl-iminooxyacetic acid,
1-(4-chlorobenzyl)-3-(t-butylthio)-5-(2-quinolinemethoxy)indol-2-yl-(2,2-dimethyl)prop-3-yl-iminooxy-2-propionic acid,
1-(4-chlorobenzyl)-3-(t-butylthio)-5-(2-pyridylmethoxy)indol-2-yl-(2,2-dimethyl)prop-3-yliminoxyacetic acid,
1-(4-chlorobenzyl)-3-(t-butylthio)-5-(4-thiazolylmethoxy)indol-2-yl-(2,2-dimethyl)prop-3-yliminooxyacetic acid,
1-(4-chlorobenzyl)-3-(t-butylthio)-5-(4-thiazolylmethoxy)indol-2- yl-(2,2-dimethyl)prop-3-yliminooxy-2-propionic acid,
1-(4-fluorobenzyl)-3-(t-butylthio)-5-(2-quinolinylmethoxy)indol-2-yl-(2,2-dimethyl)prop-3-yliminooxyacetic acid, 1-(4-chlorobenzyl)-3-(t-butylthio)-5-(2-quinolinylmethoxy)indol-2-ylmethyliminooxyacetic acid, 1-(4-chlorobenzyl)-3-(t-butylthio)-5-(2-quinolinylmethoxy)indol-2-ylmethyliminooxy-2-propionic acid, and 1-(4-chlorobenzyl)-3-(t-butylthio)-5-(2-benzothiazoylmethoxy)indol-2-yl=(2,2-dimethyl)prop-3-yliminooxyacetic acid.

Certain compounds of this invention may exist in either cis or trans or E or Z isomers with respect to the oxime geometry and in addition to stereoisomeric forms by virtue of one or more chiral centers. The present invention comtemplates all such geometric and stereoisomers, including R- and S-enantiomers, diastereomers, and cis/trans or E/Z mixtures thereof as falling within the scope of the invention. If a particular enantiomer is desired, it may be prepared by asymmetric synthesis or by derivitization with a chiral auxiliary and the resulting diastereomeric mixture separated and the auxiliary group cleaved to provide the pure enantiomers.

Inhibition of Leukotriene Biosynthesis In Vitro

Inhibition of leukotriene biosynthesis was evaluated in assays, involving calcium ionophore-induced $LTB_4$ biosynthesis expressed by human polymorphonuclear leukocytes (PMNL) or human whole blood. Human PMNL were isolated from heparinized (20 USP units/mL) venous blood using Ficoll-Hypaque Mono-Poly Resolving Medium. Human PMNL suspensions ($5 \times 10^6$ cells/250 $\mu$L) were preincubated with test compounds or vehicle for 15 min at 37° C. followed by calcium ionophore A23187 challenge (final concentration of 8.3 $\mu$M) and the reaction terminated after 10 min by adding two volumes of methanol containing prostaglandin $B_2$ as an internal recovery standard. The methanol extracts were analyzed for $LTB_4$ content by HPLC. The compounds of this invention inhibit leukotriene biosynthesis as illustrated in Table 1.

TABLE 1

| Inhibition of $LTB_4$ Biosynthesis in Human PMNL | |
|---|---|
| Example | Human PMNL $IC_{50}$ ($\mu$M) |
| 1 | 0.010 |
| 2 | 0.010 |
| 5 | 0.008 |
| 6 | 0.005 |

Inhibition of Leukotriene Biosynthesis In Vivo

Inhibition of the biosynthesis of leukotrienes in vivo after oral administration of compound was determined using a rat peritoneal anaphylaxis model in a similar manner as that described by Young and coworkers (Young, P. R.; Dyer, R. D.; Carter, G. W. *Fed. Proc., Fed. Am. Sec. Exp. Biol.* 1985, 44, 1185). In this model rats were injected intraperitoneally (ip) with rabbit antibody to bovine serum albumin (BSA) and three hours later injected ip with BSA to induce an antigen-antibody response. Rats were sacrificed 15 minutes after this challenge and the peritoneal fluids were collected and analyzed for leukotriene levels. Test compounds were administered by gavage one hour prior to the antigen challenge. Percent inhibition values were determined by comparing the treatment group to the mean of the control group. The product of example 1 inhibits leukotriene biosynthesis with an $ED_{50}$ of 0.90 mg/kg po, thus, demonstrating that compounds of this invention are orally effective in preventing the in vivo biosynthesis of leukotrienes.

Pharmaceutical Compositions

The present invention also provides pharmaceutical compositions which comprise compounds of the present invention formulated together with one or more non-toxic pharmaceutically acceptable carders. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracistemally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carders, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drag to polymer and the nature of the particular polymer employed, the rate of drag release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agaragar, and tragacanth, and mixtures thereof.

Compositions for rectal or vaginal administration are preferably suppositories which can be prepared by mixing the compounds of this invention with suitable non-irritating excipients or carders such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

The compounds of the present invention are synthesized by the following general synthetic routes. The following abbreviations are used: THF for tetrahydrofuran, DMSO for dimethylsulfoxide, n-BuLi for n-butyllithium, DCC for dicyclohexyl carbodiimide, DEAD for diethyl azodicarboxylate, DMF for N,N-dimethylformamide, DIAD for diisopropyl azodicarboxylate, and $CDCl_3$ for deuterochloroform, DMSO-$d_6$ for deuterodimethylsulfoxide.

The compounds of this invention are prepared by the general synthetic process outlined Scheme 1. Treatment of the requisite substituted phenylhydrazine hydrochloride 1 with the alkylating agent $R_2X$, where X is a leaving group such as halogen or methansulfonate in the presence of a suitable base provides the intermediate substituted hydrazine 2. A Fisher-indole reaction provides condensation of intermediate 2 with the requisite ketoester intermediate 3 to yield the substituted indole derivative 4. Reduction of the ester function by standard methods provides the hydroxy intermediate 5. Reaction of intermediate 5 with N-hydroxyphthalimide under standard Mitsunobu reaction conditions provides the N-phthaloyl intermediate which was deprotected with hydrazine hydrate to provide the O-substituted hydroxylamine intermediate 6. Reaction of 6 with the requisite keto-intermediate 7 in the presence of acetic acid affords the desired compound.

from 4-methoxyphenylhydrazine 8 as described in Scheme 1 above. Demethylation of intermediate 10 with aluminum chloride in t-butyl mercaptan and subsequent ether formation by reaction of the 5-hydroxyindole intermediate with QX where X is a leaving group such as halogen or mesylate and Q is selected from alkyl, optionally substituted aryl or arylalkyl, and optionally substituted heteroaryl or heteroarylalkyl, provides the intermediate indole 11. The desired compound II is then prepared from 11 as described in Scheme 1 above.

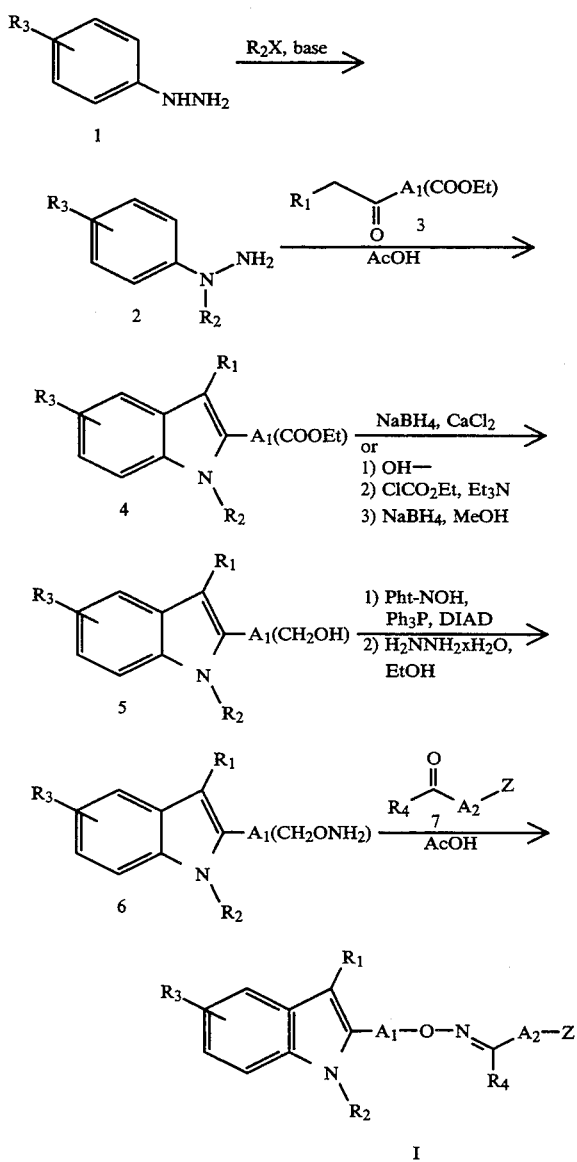

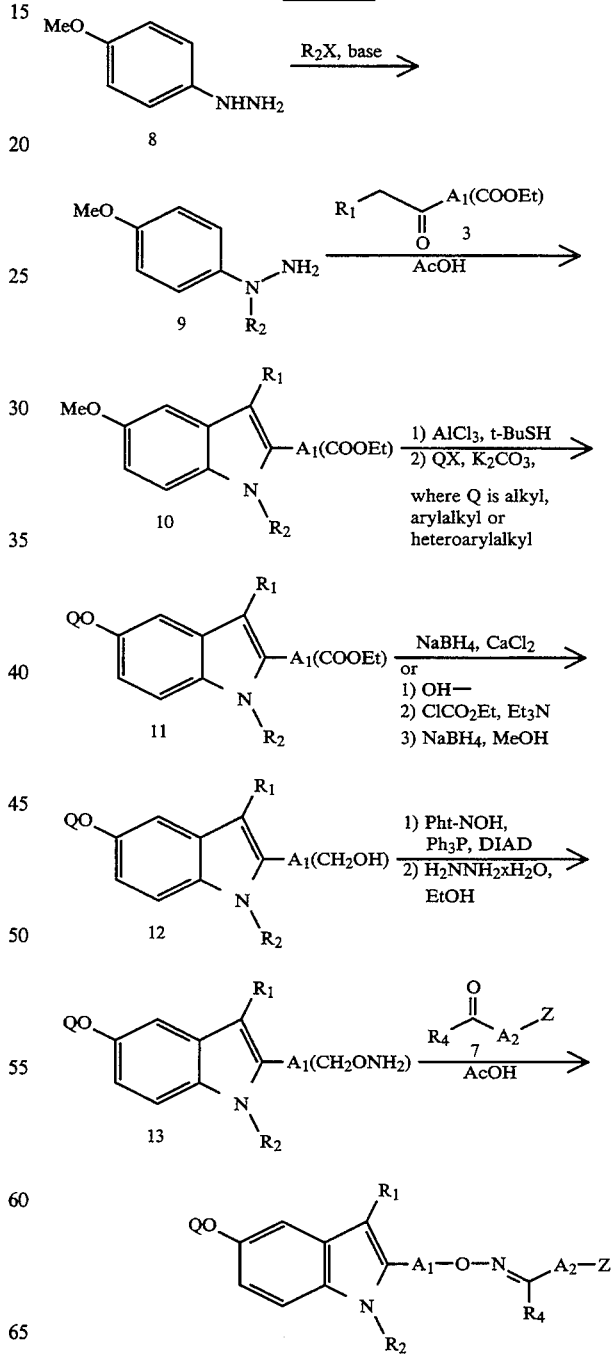

The compounds of this invention in which $R_3$ is alkoxy, optionally substituted aryloxy or arylalkoxy, or optionally substituted heteroaryloxy or heteroarylalkoxy, are prepared by the synthetic process outlined in Scheme 2. Methoxyindole derivative 10 is prepared The compounds of Formula III are prepared by the synthetic process outlined in Scheme 3. Treatment of 4-methoxyphenylhydrazine hydrochloride 14 with 4-fluorophenylmethylchloride in the presence of an amine base followed by a Fisher-indole reaction with keto-ester 15 provides the methoxyindole derivative 16. O-substituted hydroxylamine intermediate 19 is prepared from 16 as described in Scheme 2 above. Reaction of 19 with the requisite keto-acid 20 in the presence of acetic acid affords the desired compound.

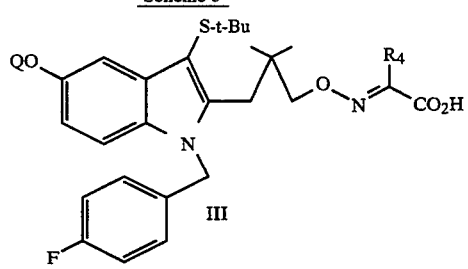

The compounds of Formula IV, in which $A_1$ is methylene, are prepared by the synthetic process outlined in Scheme 4. Treatment of 4-methoxyphenylhydrazine hydrochloride 14 with 4-chlorophenylmethylchloride in the presence of a diethylamine followed by a Fisher-indole reaction with ketoester 21 provides the methoxyindole derivative 22, which is then converted to O-substituted hydroxylamine intermediate 25 as described in Scheme 2 above. Reaction of 25 with the requisite keto-acid 20 in the presence of acetic acid affords the desired compound of Formula IV.

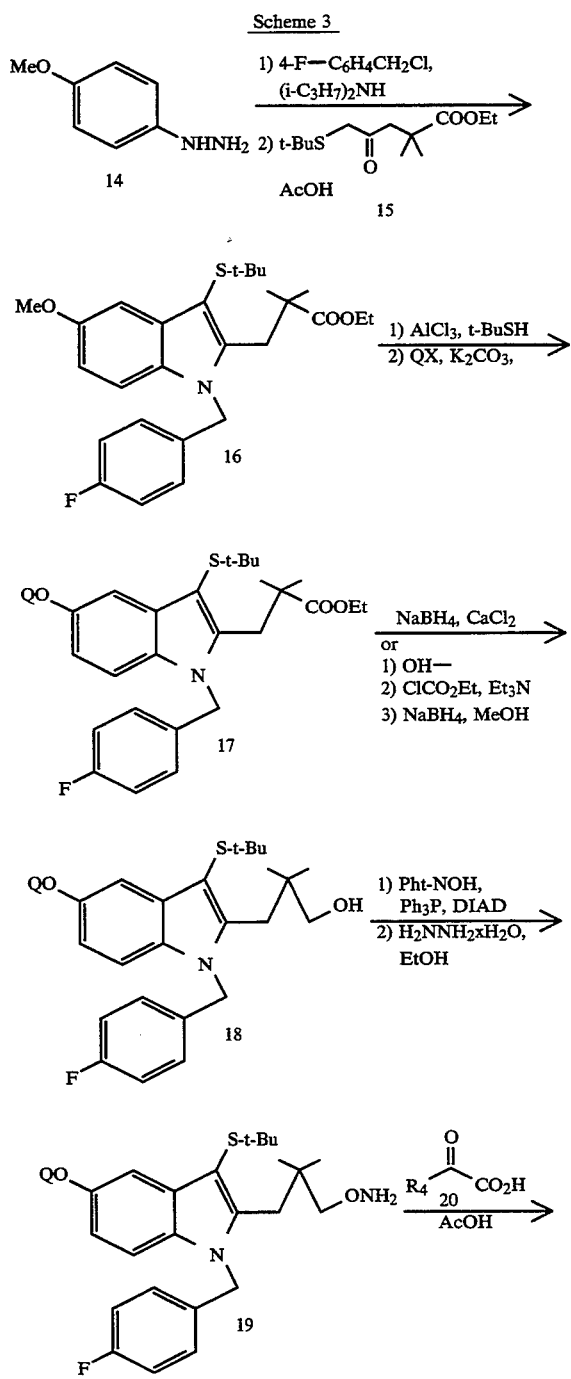

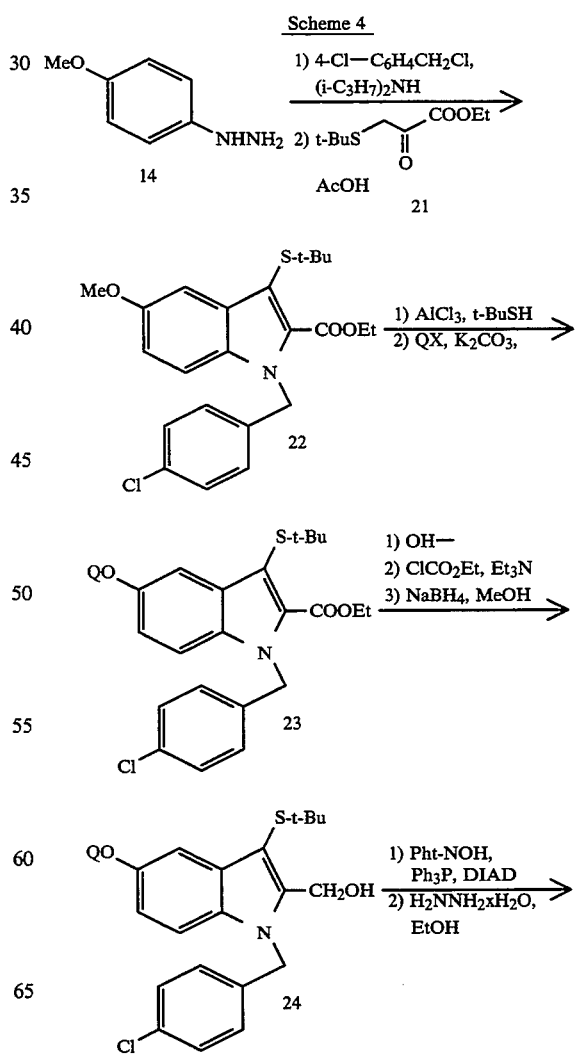

-continued
Scheme 4

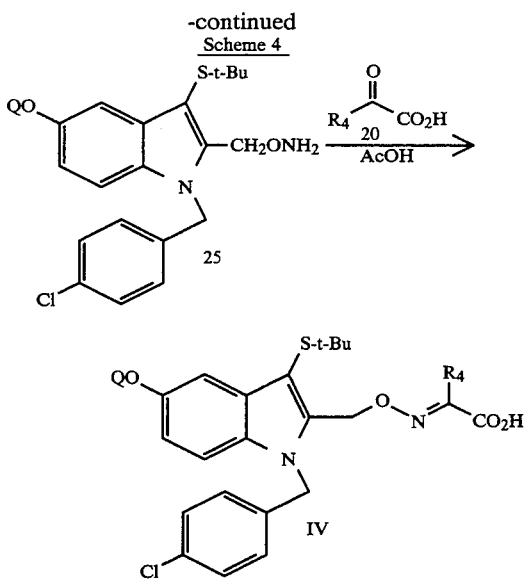

The foregoing may be better illustrated by the following Examples, which are presented for purposes of illustration and are not intended to limit the scope of the invention.

Example 1

Preparation of 1-(4-chlorobenzyl)-3-(t-butylthio)-5-(2-quinolinemethoxy))indol-2-yl-(2,2-dimethyl)prop-3-yl-iminooxyacetic acid Step 1: 1-(4-chlorobenzyl)1-(4-methoxyphenyl)hydrazine To a suspension under $N_2$ of 4-methoxyphenylhydrazine hydrochloride (41 g, 230 mmol) in methylene chloride (1000 ml) were added diisopropylamine (79.8 g, 612 mmol), 4-chlorobenzyl chloride (40.25 g, 250 mmol) and tetrabutylammonium bromide (22.8 g, 70 mmol), and the resulting mixture was stirred at room temperature for 48 hours. The reaction mixture was then washed with water and brine, dried over $MgSO_4$, filtered, and concentrated in vacuo. The residue was purified by chromatography on silica gel (2.5% methanol/methylene chloride), followed by washing of the solid with 10% ethyl ether in hexane and drying in vacuo to provide 43.5 g of 1-(4-chlorobenzyl)-1-(4-methoxyphenyl)hydrazine. mp.55° C.

Step 2: ethyl 3-[1-(4-chlorobenzyl)-3-(t-butylthio)-5-methoxyindol-2-yl]-2,2-dimethylpropionate To a mixture of 1-(4-chlorobenzyl)-1-(4-methoxyphenyl)hydrazine (38.25 g; 150 mmol), prepared as in step 1, in toluene (250 ml) was added acetic acid (175 ml) and ethyl 5-t-butylthio-2,2-dimethyl-4-oxo-pentanoate (38.2 g, 150 mmol) and the resulting mixture was stirred in the dark and at ambient temperature for 96 hours. The reaction mixture was diluted with $H_2O$ and the layers were separated. The organic layer was washed with water and brine, dried over $MgSO_4$, filtered, and concentrated in vacuo. The residue was purified by chromatography on silica gel (hexane/ethyl acetate, 4:1) to provide 36.5 g of ethyl 3-(1-(4-chlorobenzyl)-3-(t-butylthio)-5-methoxyindo-2-yl)-2,2-dimethylpropionate.

Step 3: 3-(1-(4-chlorobenzyl)-3-(t-butylthio)-5-hydroxyindol-2-yl)-2,2-dimethylpropionate To a suspension of aluminum chloride (26.3 g, 198 mmol) in t-butanethiol (60 ml) at 0° C. was added a solution of ethyl 3-(1-(4-chlorobenzyl)-3-(t-butylthio)-5-methoxyindol-2-yl)-2,2-dimethylpropionate (32 g, 66 mmol), prepared as in step 2, in methylene chloride (90 ml) and the reaction mixture was stirred at 0° C. for 10 min and at ambient temperature for 3 hours. The reaction mixture was then poured into ice and acidified with 10% aqueous hydrochloric acid. The organic layer was washed with water and brine, dried over $MgSO_4$, filtered, and concentrated in vacuo to provide a white solid. The solid was washed with 20% solution of ethyl ether in hexane and dried in vacuo to afford 21.8 g of ethyl 3-(1-(4-chlorobenzyl)-3-(t-butylthio)-5-hydroxyindol-2-yl)-2,2-dimethylpropionate.

Step 4: ethyl 3-(1-(4-chlorobenzyl)-3-(t-butylthio)-5-(2-quinolinemethoxy)-indol-2-yl)-2,2-dimethylpropionate A mixture of chloromethylquinoline hydrochloride (1.07 g, 5 mmol), $K_2CO_3$ (2.07 g, 15 mmol) and ethyl 3-(1-(4-chlorobenzyl)-3-(t-butylthio)-5-hydroxyindol-2-yl)-2,2-dimethylpropionate (2.37 g; 5 mmol), prepared as in step 3, in anhydrous DMF (30 ml) was refluxed at 60° C. for 3 hours and stirred at ambient temperature for 15 hours. The reaction mixture was poured into water and extracted with ethyl acetate (80 ml). The organic phase was dried over $MgSO_4$, filtered, and concentrated in vacuo to provide 2.6 g of ethyl 3-(1-(4-chlorobenzyl)-3-(t-butylthio)-5-(2-quinolinemethoxy)-indol-2-yl)-2,2-dimethylpropionate.

Step 5: 3-(1-(4-chlorobenzyl)-3-(t-butylthio)-5-(2-quinolinemethoxy)-indol-2-yl)-2,2-dimethylpropan-1-ol To a 0° C. solution of ethyl 3-(1-(4-chlorobenzyl)-3-(t-butylthio)-5-(2-quinolinemethoxy)-indol-2-yl)-2,2-dimethylpropionate (2.5 g; 4 mmol), prepared as in step 4, in ethanol (30 ml) and THF (20 ml) were added under a stream of $N_2$ powdered calcium chloride (0.90 g, 8.0 mmol) and sodium borohydride (0.60 g, 16 mmol) and the resulting mixture was stirred at 0° C. for 2 hours and at ambient temperature for 14 hours. The reaction mixture was neutralized with 6N aqueous hydrochloric acid and extracted with ethyl acetate. The organic extract was washed with water and brine, dried over $MgSO_4$, filtered, and concentrated in vacuo to provide 2.3 g of 3-(1-(4-chlorobenzyl)-3-(t-butylthio)-5-(2-quinolinemethoxy)-indol-2-yl)-2,2-dimethylpropan-1-ol.

Step 6: N-phthaloyl-O-((3-(1-(4-chlorobenzyl)-3-(t-butylthio)-5-(2-quinolinemethoxy)-indol-2-yl)-2,2-dimethylpropyl)hydroxylamine To a solution of 3-(1-(4-chlorobenzyl)-3-(t-butylthio)-5-(2-quinolinemethoxy)-indol-2-yl)-2,2-dimethylpropan-1-ol (2.3 g, 4 mmol), prepared as in step 5, N-hydroxyphthalimide (0.75 g, 4.5 mmol) and triphenylphosphine (1.31 g, 5.0 mmol) in THF (100 ml) was added dropwise diisopropylazodicarboxylate (1.01 g, 5.0 mmol) and the resulting mixture was stirred at room temperature for 2 hours. The reaction mixture was concentrated in vacuo and the residue was purified by chromatography on silica gel (5% ethyl acetate/$CH_2Cl_2$) to provide N-phthaloyl-O-((-3-(1-(4-chlorobenzyl)-3-(t-butylthio)-5-(2-quinolinemethoxy)-indol-2-yl)-2,2-dimethylpropyl)hydroxylamine.

Step 7:
O-((3-(1-(4-chlorobenzyl)-3-(t-butylthio)-5-(2-quinolinemethoxy)-indol-2-yl)-2,2-dimethylpropyl)hydroxylamine A mixture of N-phthaloyl-O-((3-(1-(4-chlorobenzyl)-3-(t-butylthio)-5-(2-quinolinemethoxy)-indol-2-yl)-2,2-dimethylpropyl)hydroxylamine from step 6 above and hydrazine hydrate (1 ml) in ethanol was refluxed for 1 hour and then concentrated in vacuo. The residue was partitioned between $CH_2Cl_2$ and 10% aqueous sodium carbonate, and the organic layer was washed with water and brine, dried over $MgSO_4$, filtered, and concentrated in vacuo to provide 1.75 g of O-((3-(1-(4-chlorobenzyl)-3-(t-butylthio)-5-(2-quinolinemethoxy)-indol-2-yl)-2,2-dimethylpropyl)hydroxylamine.

Step 8:1-(4-chlorobenzyl)-3-(t-butylthio)-5-(2-quinolinemethoxy))indol-2-yl-(2,2-dimethyl)prop-3-yl-iminooxyacetic acid To a solution of O-((3-(1-(4-chlorobenzyl)-3-(t-butylthio)-5-(2-quinolinemethoxy)-indol-2-yl)-2,2-dimethylpropyl)hydroxylamine (700 mg, 1.3 mmol), prepared as in step 7, in THF (35 ml) and water (10 ml), were added glyoxylic acid (240 mg, 2.6 mmol) and acetic acid (0.2 ml) and the resulting mixture was stirred at room temperature for 14 hours. The organics were then removed in vacuo and the residue was diluted with water to obtain a solid. The solid was purified by chromatography on silica gel (10% methanol/$CH_2Cl_2$) to provide 420 mg of 1-(4-chlorobenzyl)-3-(t-butylthio)-5-(2-quinolinemethoxy))indol-2-yl-(2,2-dimethyl)prop-3-yl-iminooxyacetic acid. mp. 152°–155° C. $^1$H NMR (300 MHz, DMSO-$d_6$) δ: 0.87 (s, 6H), 0.97 (s, 9H), 2.90(m, 2H), 3.83 (s, 2H), 5.39 (s, 2H), 5.53 (s, 2H), 6.83 (m, 3H), 7.13 (d, 1H, J=3 Hz), 7.30 (m, 3H), 7.40 (s, 1H), 7.65 (m, 2H), 7.78 (m, 1H), 7.95 (d, 1H, J=8 Hz), 8.05 (d, 1H, J=8 Hz), 8.35 (d, 1H, J=8Hz). MS (DCI/$NH_3$) m/e 644 (M+H)$^+$. Analysis calcd. for $C_{36}H_{38}ClN_3O_4S \cdot 2HO$: C, 63.52; H, 5.88; N, 6.17. Found: C, 63.04; H, 5.95; N, 5.88.

Example 2

Preparation of 1-(4-chlorobenzyl)-3-(t-butylthio)-5-(2-quinolinemethoxy)indol-2-yl(2,2-dimethyl)prop-3-yl-iminooxy-2-propionic acid A mixture of O-(1-(4-chlorobenzyl)-3-(t-butylthio)-5-(2-quinolinemethoxy)indol-2-yl-(2,2-dimethyl)prop-3-yl)hydroxylamine (700 mg, 1.3 mmol), prepared as in Example 1, step 8, methyl pyruvate (265 mg, 2.6 mmol) and acetic acid (0.2 ml) in methanol (20 ml), THF (35 ml) and $H_2O$ (10 ml) was stirred at room temperature for 12 hours. The reaction mixture was then concentrated in vacuo and the residue was taken up in ethyl acetate and the layers were separated. The organic phase was concentrated in vacuo, and the residue was dissolved in methanol (25 ml) and treated with 1N aqueous sodium hydroxide (3 ml) for 14 hours at ambient temperature. The methanol was removed in vacuo and the residue was acidified with aqueous 6N hydrochloric acid. The product was extracted with ethyl acetate and purified by chromatography on silica gel (10% methanol/$CH_2Cl_2$) followed by crystallization from ethyl acetate/hexane to provide 375 mg of 1-(4-chlorobenzyl)-3-(t-butylthio)-5-(2-quinolinemethoxy)indol-2-yl-(2,2-dimethyl)prop-3-yl-iminooxy-2-propionic acid. mp. 145°–147° C. $^1$H NMR (300 MHz; DMSO-$d_6$) δ0.89 (s, 6H), 0.97 (s, 9H), 1.85 (s, 3H), 2.95 (m, 2H), 3.86 (s, 2H), 5.40 (s, 2H), 5.52 (s, 2H), 6.80 (d, 1H, J=8 Hz), 6.86 (dd, 1H, J=9,3 Hz), 7.14 d, 1H, J=3 Hz), 7.30 (m, 3H), 7.62 (m, 2H), 7.78 (m, 1H), 7.95 (d, 1H, J=8 Hz), 8.05 (d, 1H, J=8 Hz), 8.35 (d, 1H, J=8 Hz). MS (DCI/$NH_3$) m/e 658 (M+H)$^+$. Analysis calcd. for $C_{37}H_{40}ClN_3O_4S \cdot 2H_2O$: C, 64.06; H, 6.14; N, 6.06. Found: C, 63.56;H, 5.70; N6.01.

Example 3

Preparation of 1-(4-chlorobenzyl)-3-(t-butylthio)-5-(2-pyridylmethoxy)indol-2-yl(-2,2-dimethyl)prop-3-yliminooxyacetic acid The desired material was prepared according to the procedure of Example 1, except substituting 2-chloromethylpyridine hydrochloride for 2-chloromethylquinoline hydrochloride. $^1$H NMR (300 MHz, DMSO-$d_6$) δ 0.91 (s, 6H), 1.10 (s, 9H), 2.93 (m, 2H), 3.85 (s, 2H), 5.20 (s, 2H), 5.53 (s, 2H), 6.83 (d, 3H, J=9 Hz), 7.09 (d, 1H, J=3 Hz), 7.32 (m, 4H), 7.41 (s, 1H), 7.49 (d, 1H, J=8 Hz), 7.79 (m, 1H), 8.56 (m, 1H). MS (DCI/$NH_3$) m/e 594 (M+H)$^+$. Analysis calcd. for $C_{32}H_{36}ClN_3O_4S \cdot 2H_2O$: C, 60.95; H, 6.20; N, 6.66. Found: C, 60.74; H, 5.89; N, 6.54.

Example 4

Preparation of 1-(4-chlorobenzyl)-3-(t-butylthio)-5-(4-thiazolylmethoxy)indol-2-yl(2,2-dimethyl)prop-3-yliminooxyacetic acid The desired material was prepared according to the procedure of Example 1, except substituting 4-chloromethylthiazole for 2-chloromethylquinoline. mp. 125° C. $^1$H NMR (300 MHz, DMSO-$d_6$) δ 0.92 (s, 6H), 1.15 (s, 9H), 2.95 (m, 2H), 4.05 (s, 2H), 5.22 (s, 2H), 5.53 (s, 2H), 6.85 (m, 3H), 7.18 (d, 1H J=3 Hz), 7.31 (m, 3H), 7.58 (s, 1H), 7.73 (s, 1H), 9.13 (s, 1H); MS (FAB(−)) m/e 598 (M−1). Analysis calcd. for $C_{30}H_{34}ClN_3O_4S_2$: C, 59.89; H, 5.68; N, 6.99. Found: C, 59.31; H, 5.49; N, 6.81.

Example 5

Preparation of 1-(4-chlorobenzyl)-3-(t-butylthio)-5-(4-thiazolylmethoxy)indol-2-yl-(2,2-dimethyl)prop-3-yliminooxy-2-propionic acid The desired material was prepared according to the procedure of Example 2, except substituting 4-chloromethylthiazole for 2-chloromethylquinoline. mp. 110° C. $^1$H NMR (300 MHz, DMSO-$d_6$) δ 0.95 (s, 6H), 1.15 (s, 9H), 1.93 (s, 3H), 3.0 (m, 2H), 4.05 (s, 2H), 5.22 (s, 2H), 5.53 (s, 2H), 6.83 (m, 3H), 7.18 (d, 1H, J=3 Hz), 7.30 (m, 3H), 7.72 (d, 1H, J=1.5 Hz), 9.12 (d, 1H, J=1.5 Hz). MS (DCI/$NH_3$) m/e 614 (M+H)$^+$.

Example 6

Preparation of
1-(4-fluorobenzyl)-3-(t-butylthio)-5-(2-quinolinylmethoxy)indol-2-yl-(2,2-dimethyl)prop-3-yliminooxyacetic acid.

The desired material was prepared according to the procedure of Example 1, substituting 4-fluorobenzyl chloride for 4-chlorobenzyl chloride. mp. 142°–145° C. $^1$H NMR (300 MHz, DMSO-$d_6$) δ 0.90 (s, 6H), 0.98 (s, 9H), 2.90 (m, 2H), 3.83 (s, 2H), 5.39 (s, 2H), 5.49 (s, 2H), 6.85 (m, 3H), 7.09 (m, 3H), 7.31 (d, 1H, J = 8 Hz), 7.40 (s, 1H), 7.63 (m, 2H), 7.78 (m, 1H), 7.96 (d, 1H, J=8 Hz), 8.05 (d, 1H J=8 Hz), 8.36 (d, 1H, J=8 Hz). MS (DCI/NH$_3$) m/e 628 (M+H)$^+$. Analysis calcd. for $C_{36}H_{38}FN_3O_4S \cdot H_2O$: C, 66.93; H, 6.21; N, 6.45. Found: C, 66.94; H, 6.31; N, 6.15.

Example 7

Preparation of
1-(4-chlorobenzyl)-3-(t-butylthiol)-5-(2-quinolinylmethoxy)indol-2-ylmethyliminooxyacetic acid Step 1: ethyl
5-methoxy-3-(t-butylthio)indole-2-carboxylate.

A mixture of 4-methoxyphenylhydrazine hydrochloride (5.95 g; 34 mmol) and ethyl 3-(S-t-butyl)pyruvate (7.0 g; 34 mmol) in t-butanol (70 ml) was gently refluxed for 48 hours, and then concentrated in vacuo. The residue was partitioned between H$_2$O and ethyl acetate and the organic layer was washed with water and brine, dried over MgSO$_4$, filtered, and concentrated in vacuo. The residue was purified by chromatography on silica gel (2:1 hexane/ethyl acetam) to afford 3.5 g of ethyl 5-methoxy-3-(t-butylthio)indole-2-carboxylate.

Step 2: ethyl
1-(4-chlorobenzyl)-3-(t-butylthiol)-5-methoxyindole-2-carboxylate

To a solution of ethyl 5-methoxy-3-(t-butylthio)indole-2-carboxylate from step 1 in DMF (50 ml) at 0° C. was added sodium hydride (60% suspension in mineral oil 460 mg, 11.5 mmol). The reaction mixture was stirred at room temperature for 15 minutes, and p-chlorobenzyl chloride (1.93 g, 12.0 mmol) was added. The reaction mixture was stirred at ambient temperature for 14 hours and was then poured into H$_2$O (200 ml) and extracted with ethyl acetate. The organic phase was washed with H$_2$O and brine, dried over MgSO$_4$, filtered, and concentrated in vacuo. The residue was purified by chromatography on silica gel (8:1 hexane/ethyl acetate) to provide 4.1 g of ethyl 1-(4-chlorobenzyl)-3-(t-butylthio)-5-methoxyindole-2-carboxylate.

Step 3: ethyl
1-(4-chlorobenzyl)-3-(t-butylthio)-5-hydroxyindole-2-carboxylate

To a 0° C. suspension of anhydrous aluminum chloride (4.8 g, 36 mmol) in CH$_2$Cl$_2$ (15 ml) was added t-butyl mercaptan (12 ml) followed by ethyl 1-(4-chlorobenzyl)-3-(t-butylthio)-5-methoxyindole-2-carboxylate (3.77 g; 11 mmol), prepared as in step 2, and the resulting mixture was stirred at 0° C. for 45 min. The reaction mixture was then poured into ice and aqueous 1N hydrochloric acid (100 ml) and extracted with ethyl acetate. The organic phase was concentrated in vacuo to provide 4.2 g of crude oily ethyl 1-(4-chlorobenzyl)-3-(t-butylthio)-5-hydroxyindole-2-carboxylate which was used without further purification.

Step 4: ethyl
1-(4-chlorobenzyl)-5-(2-quinolinemethoxy)-3-(t-butylthio)indole-2-carboxylate To a solution of the 1-(4-chlorobenzyl)-3-(t-butylthio)-5-hydroxyindole-2-carboxylate, prepared in step 3, in DMF (60 ml) was added K$_2$CO$_3$ (1.66 g, 12 mmol) and 2-chloromethylquinoline (2.1 g, 12 mmol), and the mixture was stirred at 50° C. for 14 hours. The reaction mixture was then partioned between H$_2$O and ethyl acetate, and the organic layer was washed with water and brine, dried over MgSO$_4$, filtered, and concentrated in vacuo. The residue was purified by chromatography on silica gel (2:1 hexane/ethyl acetate) to afford 1.7 g of ethyl 1-(4-chlorobenzyl)-5-(2-quinolinemethoxy)-3-(t-butylthio)indole-2-carboxylate and 3.0 g of 1-(4-chlorobenzyl)-5-(2-quinolinemethoxy)-3-(2-quinolinemethylthio)indole-2-carboxylate.

Step 5:
1-(4-chlorobenzyl)-3-(t-butylthio)-5-(2-quinolinemethoxy)indole-2-carboxylic acid A mixture of 1-(4-chlorobenzyl)-3-(t-butylthio)-5-(2-quinolinemethoxy)indole-2-carboxylic acid ethyl ester (1.7 g, 3 mmol), prepared as in step 4, and aqueous 1N sodium hydroxide (10 ml, 10 mmol) in dioxane (15 ml) and methanol (30 ml) was refluxed for 6 hours at 50° C. The organics were then removed in vacuo and the residue was acidified to pH 3 with 10% citric acid. The solid was filtered and dried in vacuo to afford 1.15 g of 1-(4-chlorobenzyl)-3-(t-butylthio)-5-(2-quinolinemethoxy)indole-2-carboxylic acid.

Step 6:
1-(4-chlorobenzyl)-3-(t-butylthio)-5-(2-quinolinemethoxy)-2-hydroxymethylindole To a −15° C. solution of 1-(4-chlorobenzyl)-3-(t-butylthio)-5-(2-quinolinemethoxy)indole-2-carboxylic acid (360 mg, 0.66 mmol), prepared as in step 5, in THF (20 ml) was added triethylamine (0.10 ml, 0.70 mmol), followed by dropwise addition of ethyl chloroformate (0.07 ml; 0.70 mmol). The reaction mixture was stirred at −15° to −10° C. for 20 min. and then sodium borohydride (76 mg, 2.0 mmol) was added. The reaction mixture was warmed to 0° C. and methanol (10 ml) was added over a period of 20 min. The reaction mixture was acidified to pH 4 and extracted with ethyl acetate (70 ml). The organic phase was washed with H$_2$O and brine and concentrated in vacuo to provide 340 mg of 1-(4-chlorobenzyl)-3-(t-butylthio)-5-(2-quinolinemethoxy)-2-hydroxymethylindole.

Step 7:
N-phthaloyl-O-(1-(4-chlorobenzyl)-3-(t-butylthio)-5-(2-quinolinemethoxy)indol-2-ylmethyl)hydroxylamine To a solution under N$_2$ of the 1-(4-chlorobenzyl)-3-(t-butylthio)-5-(2-quinolinemethoxy)-2-hydroxymethylindole prepared in step 6 in THF (25 ml) at ambient temperature was added triphenylphosphine (262 mg, 1.00 mmol) and N-hydroxyphthalimide (108 mg, 0.66 mmol). Diethylazodicarboxylate (0.16 ml, 1.00 mmol) in THF (5 ml) was then added dropwise. The reaction mixture was left at ambient temperature for 15 hours and then concentrated in vacuo. The residue was purified by chromatography on silica gel (3:1 hexane/ethyl acetate)

to afford 360 mg of N-phthaloyl-O-(1-(4-chlorobenzyl)-3-(t-butylthio)-5-(2-quinolinemethoxy)indol-2-ylmethyl)hydroxylamine.

Step 8:
O-1-(4-chlorobenzyl)-3-(t-butylthio)-5-(2-quinolinemethoxy)indol-2-ylmethyl)hydroxylamine A mixture of N-phthaloyl-O-(1-(4-chlorobenzyl)-3-(t-butylthio)-5-(2-quinolinemethoxy)indol-2-ylmethyl)hydroxylamine (300 mg, 0.435 mmol), prepared as in step 7, and hydrazine hydrate (0.05 ml, 0.90 mmol) in ethanol (10 ml) and dioxane (5 ml) was refluxed for 30 min and then cooled to ambient temperature. 10% Aqueous sodium carbonate was added and the mixture was extracted with ethyl acetate. The organic phase was concentrated in vacuo to afford 240 mg of crude O-(1-(4-chlorobenzyl)-3-(t-butylthio)-5-(2-quinolinemethoxy)indol-2-ylmethyl)hydroxylamine which was used without further purification.

Step 9:
1-(4-chlorobenzyl)-3-(t-butylthio)-5-(2-quinolinylmethoxy)indol-2-ylmethyliminooxyacetic acid To a solution of the O-1-(4-chlorobenzyl)-3-(t-butylthio)-5-(2-quinolinemethoxy)indol-2-ylmethyl)hydroxylamine prepared in step 8 in methanol (25 ml) were added glyoxylic acid (92 mg, 1.0 mmol) and acetic acid (0.06 ml, 1.0 mmol) and the resulting mixture was stirred at room temperature for 14 hours. The reaction mixture was poured into $H_2O$ and extracted with ethyl acetate. The organic layer was washed with $H_2O$ and brine, dried over $MgSO_4$, filtered, and concentrated in vacuo. The residue was purified by chromatography on silica gel (4:1 $CH_2Cl_2$/ethanol) to afford 100 mg of 1-(4-chlorobenzyl)-3-(t-butylthio)-5-(2-quinolinylmethoxy)indol-2-ylmethyliminooxyacetic acid. mp 155°–157° C. $^1$H NMR (300 MHz; DMSO-$d_6$) δ 1.00 (s, 9H), 5.32 (s, 2H), 5.42 (s, 2H), 5.5 (s, 2H), 7.01 (m, 3H), 7.16 (d, 1H, J=3 Hz), 7.19 (s, 1H), 7.33 (m, 3H), 7.62 (m, 2H), 7.79 (m, 1H), 7.96 (d, 1H, J=8 Hz), 8.04 (d, 1H, J=-8 Hz), 8.35 (d, 1H, J=8 Hz). MS (FAB(+)) m/e 588 (M+1).

Example 8

Preparation of 1-(4-chlorobenzyl)-3-(t-butylthio)-5-(2-quinolinylmethoxy)indol-2-ylmethyliminooxy-2-propionic acid

Step 1: methyl 1-(4-chlorobenzyl)-3-(t-butylthio)-5-(2-quinolinylmethoxy)indol-2-ylmethyliminooxy-2-propionate A mixture of O-(1-(4-chlorobenzyl)-3-(t-butylthio)-5-(2-quinolinemethoxy)indol-2-ylmethyl)hydroxylamine (266 mg; 0.5 mmol), prepared as in Example 7, step 8, methyl pyruvate (0.06 ml, 0.60 mmol) and acetic acid (0.035 ml, 0.60 mmol) in dioxane (10 ml), methanol (10 ml) and $H_2O$ (2 ml) was stirred at ambient temperature for 12 hours. The organic solvents were then removed in vacuo and the residue was dissolved in ethyl acetate (75 ml). The organic solution was washed with $H_2O$ and brine, dried over $MgSO_4$, filtered, and concentrated in vacuo. The residue was purified by chromatography on silica gel (3:1 hexane/ethyl acetate) to afford 240 mg of methyl 1-(4-chlorobenzyl)-3-(t-butylthio)-5-(2-quinolinylmethoxy)indol-2-ylmethyliminooxy-2-propionate.

Step 2:
1-(4-chlorobenzyl)-3-(t-butylthio)-5-(2-quinolinylmethoxy)indol-2-ylmethyliminooxy-2-propionic acid To a solution of the methyl 1-(4-chlorobenzyl)-3-(t-butylthio)-5-(2-quinolinylmethoxy)indol-2-ylmethyliminooxy-2-propionate prepared in step 1 in dioxane (6 ml) and methanol (6 ml) was added aqueous 1N sodium hydroxide (2 ml) and the resulting mixture was stirred at 50° C. for 1 hour. The organics were then removed in vacuo, and the residue was diluted with water (50 ml) and acidified with 10% citric acid to pH 3. The resulting solid was filtered, washed with $H_2O$, dried under reduced pressure and recrystallized from ethyl ether-hexane to provide 150 mg of 1-(4-chlorobenzyl)-3-(t-butylthio)-5-(2-quinolinylmethoxy)indol-2-ylmethyliminooxy-2-propionic acid. mp. 135°–137° C. (decomp.). $^1$H NMR (300 MHz, DMSO-$d_6$) δ 1.02 (s, 9H), 1.53 (s, 3H), 5.42 (s, 2H), 5.52 (s, 2H), 5.57 (s, 2H), 6.93 (d, 2H, J=9 Hz), 7.0 (dd, 1H, J=9, 3 Hz), 7.2 (d, 1H, J=3 Hz), 7.34 (m, 3H), 7.65 (m, 2H), 7.8 (m, 1H), 7.96 (dd, 1H, J=8, 2 Hz), 8.05 (d, 1H, J=8 Hz), 8.36 (d, 1H, J=8 Hz). MS (DCI, NH3) m/e 602 (M+H)+. IR (in $CDCl_3$): 3440, 1760, 1710, 1620, 1600 cm$^{-1}$. Analysis calcd. for $C_{33}H_{32}ClN_3O_4S$: C, 65.82; H, 5.36; N, 6.98. Found: C, 65.49; H, 5.30; N, 6.74.

Example 9

Preparation of 1-(4-chlorobenzyl)-3-(t-butylthio)-5-(2-benzothiazoylmethoxy)indol-(2.2-dimethylprop-3-yliminooxyacetic acid The desired compound was prepared according to the procedure of Example 7, except substituting 2-chloromethylbenzothiazole for 2-chloromethylquinoline. mp. 154° C. (decomp.). $^1$H NMR (300 MHz, DMSO-$d_6$) δ 0.92 (s, 6H), 1.04 (s, 9H), 2.95 (m, 2H), 4.03 (s, 2H), 5.53 (s, 2H), 5.61 (s, 2H), 6.85 (m, 3H), 7.21 (d, 1H), J=3 Hz), 7.31 (m, 3H), 7.44 (m, 1H), 7.54 (m, 1H), 7.57 (s, 1H), 8.03 (d, 1H, J=9 Hz), 8.08 (d, 1H, J=9 Hz). MS (FAB) m/e 650 (M+1). IR (in $CDCl_3$): 3440, 1760, 1710, 1620, 1600 cm$^{-1}$. Analysis calcd. for $C_{34}H_{36}ClN_3O_4S_2$: C, 62.79; H, 5.58; N, 6.46. Found: C, 62.70; H, 5.53; N, 6.30.

We claim:

1. A compound having the formula

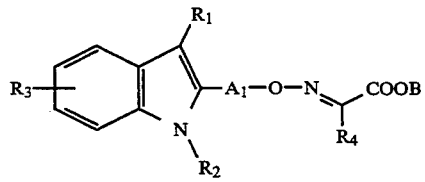

or a pharmaceutically acceptable salt thereof wherein
$A_1$ is alkenylene of one to twelve carbon atoms;
$R_1$ is alkylthio of one to six carbon atoms;
$R_2$ is selected from the group consisting of
phenylakyl in which the alkyl portion is of one to six carbon atoms, and
the phenyl group is optionally substituted with up to three substituents selected from the group consisting of
alkyl of one to six carbon atoms,
halogen, haloalkyl of one to six carbon atoms, and alkoxy of one to twelve carbon atoms;

$R_3$ is selected from the group consisting of optionally substituted heteroaryl,
wherein the heteroaryl group is selected from the group consisting of
pyridyl,
quinolyl,
thiazolyl,
benzothiazolyl,
wherein the optional substituents on the heteroaryl groups are selected from the group consisting of
alkyl of one to six carbon atoms,
halogen,
alkoxy of one to six carbon atoms, and
haloalkyl of one to six carbon atoms; and $R_4$ is selected from the group consisting of
hydrogen, and
alkyl of one to six carbons optionally substituted with hydroxy.

2. A compound or a pharmaceutically acceptable salt thereof as defined by claim 1 selected from the group consisting of
(1-(4-chlorobenzyl)-3-(t-butylthio)-5-(2-quinolinemethoxy))indol-2-yl-(2,2-dimethyl)prop-3-yl-iminooxyacetic acid,
1-(4-chlorobenzyl)-3-(t-butylthio)-5-(2-quinolinemethoxy)indol-2-yl-(2,2-dimethyl)prop-3-yl-iminooxy-2-propionic acid,
1-(4-chlorobenzyl)-3-(t-butylthio)-5-(2-pyridylmethoxy)indol-2-yl-(2,2-dimethyl)prop-3-yliminooxyacetic acid,
1-(4-chlorobenzyl)-3-(t-butylthio)-5-(4-thiazolylmethoxy)indol-2-yl-(2,2-dimethyl)prop-3-yliminooxyacetic acid,
1-(4-chlorobenzyl)-3-(t-butylthio)-5-(4-thiazolylmethoxy)indol-2-yl-(2,2-dimethyl)prop-3-yliminooxy-2-propionic acid,
1-(4-fluorobenzyl)-3-(t-butylthio)-5-(2-quinolinylmethoxy)indol-2-yl-(2,2-dimethyl)prop-3-yliminooxyacetic acid,
1-(4-chlorobenzyl)-3-(t-butylthio)-5-(2-quinolinylmethoxy)indol-2-ylmethyliminooxyacetic acid,
1-(4-chlorobenzyl)-3-(t-butylthio)-5-(2-quinolinylmethoxy)indol-2-ylmethyliminooxy-2-propionic acid, and
1-(4-chlorobenzyl)-3-(t-butylthio)-5-(2-benzothiazoylmethoxy)indole-(2,2-dimethyl)prop-3-yliminooxyacetic acid.

3. A pharmaceutical composition for inhibiting the biosynthesis of leukotrienes comprising a therapeutically effective amount of a compound as defined by claim 1 in combination with a pharmaceutically acceptable carrier.

4. A method of inhibiting the biosynthesis of leukotrienes comprising administering to a mammal in need of such treatment a therapeutically effective amount of a compound as defined by claim 1.

* * * * *

UNITED STATES PATENT AND TRADEMARK OFFICE
CERTIFICATE OF CORRECTION

PATENT NO. : 5,399,699
DATED : March 21, 1995
INVENTOR(S) : Teodozyj Kolasa; Pramila Bhatia; Dee W. Brooks It is certified that error appears in the above-indentified patent and that said Letters Patent is hereby corrected as shown below:

TITLE PAGE, COLUMN 1:   Inventors: delete "Teodozyi"
                                   insert --Teodozyj--

COLUMN 15, LINE 67:   delete "-5-methoxyindo-2-yl)"
                      insert -- -5-methoxyindol-2-yl)--

Signed and Sealed this

Fifth Day of December, 1995

Attest:

Attesting Officer

BRUCE LEHMAN

Commissioner of Patents and Trademarks